United States Patent [19]

Bollé

[11] Patent Number: 5,666,663
[45] Date of Patent: Sep. 16, 1997

[54] ADAPTER FOR PROTECTIVE MASK FOR A HELMET

[75] Inventor: Maurice Bollé, Oyonnax, France

[73] Assignee: Establissements Bolle, Oyonnax, France

[21] Appl. No.: 438,680

[22] Filed: May 10, 1995

[30] Foreign Application Priority Data

May 13, 1994 [FR] France .................... 94 05890

[51] Int. Cl.$^6$ ............... A61F 9/02; A42B 3/00
[52] U.S. Cl. ................... 2/10; 2/452
[58] Field of Search .............. 2/452, 428, 430, 2/436, 437, 439, 440, 10, 424, 425; 24/265 R

[56] References Cited

U.S. PATENT DOCUMENTS 4,176,410  12/1979  Matthias ........................ 2/436
4,264,987   5/1981  Runckel ........................ 2/248
4,556,995  12/1985  Yamamoto ..................... 2/439

FOREIGN PATENT DOCUMENTS 2224120  10/1974  France .
2539040   7/1984  France .
 735281   5/1943  Germany .
1040048   8/1966  United Kingdom .

*Primary Examiner*—Peter Nerbun
*Attorney, Agent, or Firm*—Jacobson, Price, Holman & Stern, PLLC

[57] ABSTRACT

An adapter consists of a rigid V-shaped angle piece (7), one leg (8) of which is provided with a slit (9) through which the fastening strap of a mask is fed, while the other leg (10) is equipped with hooks (11) to attach it to the side parts of the mask, in such a way that the fastening point of the strap is offset towards the front of the mask—for use with protective masks or goggles.

1 Claim, 1 Drawing Sheet

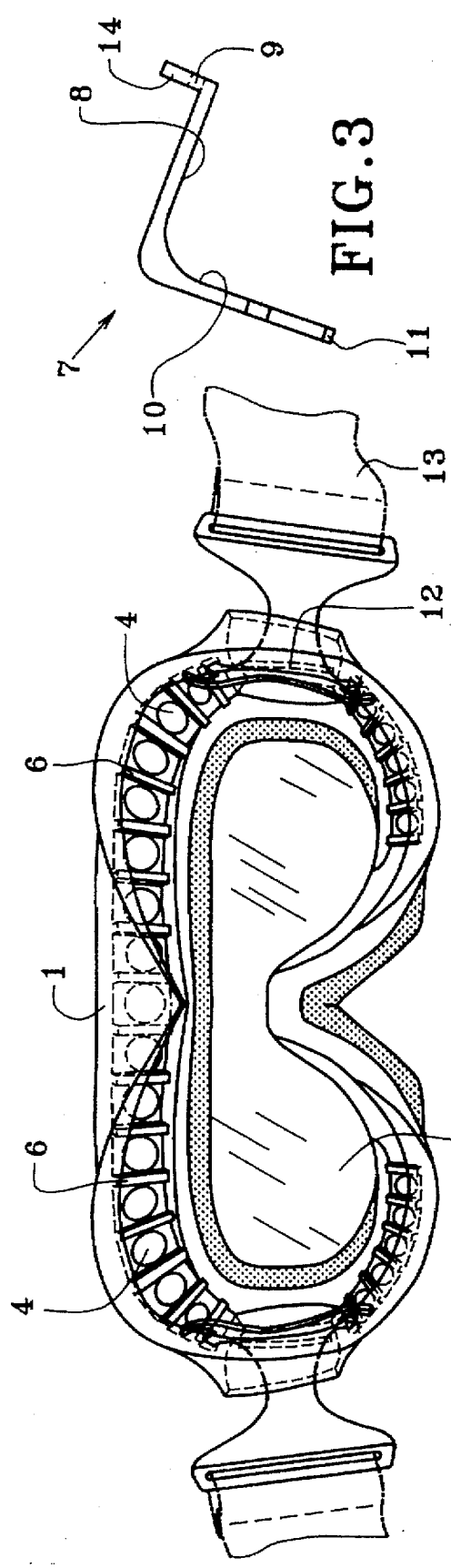
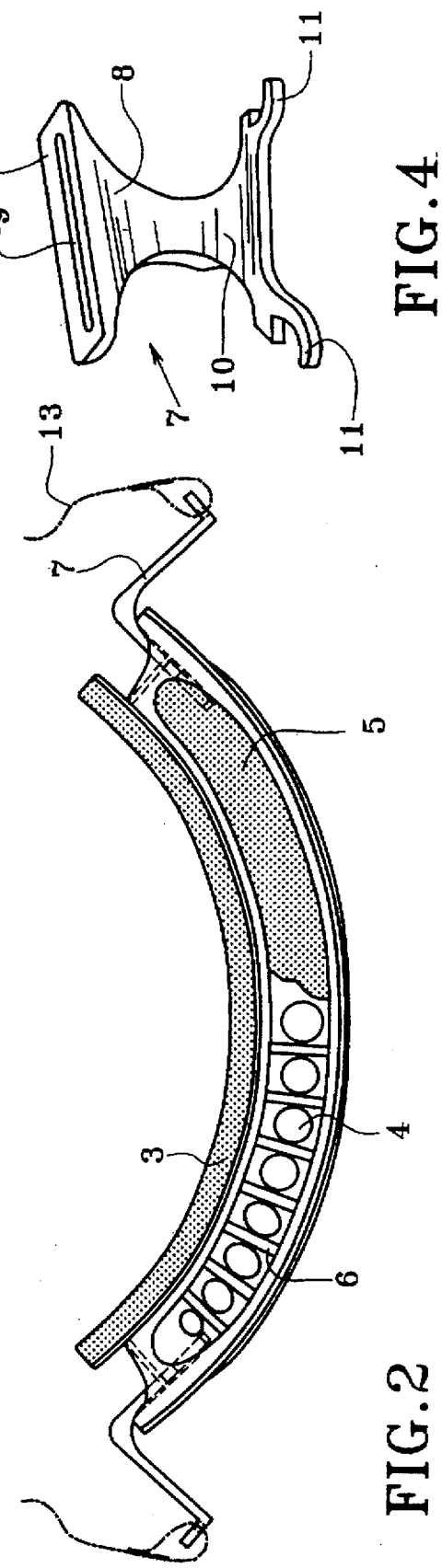

ADAPTER FOR PROTECTIVE MASK FOR A HELMET

The invention refers to a protective mask or goggles, and more specifically to an adapter allowing the protective mask to be used with a helmet.

It is well-known that a protective mask or goggles are attached to the user's head by means of a suitably flexible fastening strap which is secured directly on the side edge at each side of the mask, and goes round the back of the head. The rim of the streamlined mask is thus always in contact with the face, ensuring effective protection of the eyes, When using such a mask together with a helmet the fastening strap is placed over the helmet, which represents an extra thickness on both sides of the head. As a result, when the strap is tightened and pulls the sides of the mask outwards, the side parts are lifted off the face and no longer provide effective protection for the user. To compensate for this inconvenience the side parts of the mask in contact with the face must be extended, which increases the thickness and consequently reducing the peripheral field of vision.

As this solution is not satisfactory, the applicant has developed an adapter consisting of a joining piece which offsets the protective mask from its fastening strap. Goggles worn with the helmet thus remain correctly positioned on the face.

The object of this invention therefore is an adapter for a protective mask for a helmet which consists of a rigid V-shaped angle piece, one leg of which is fitted with a mechanism for accepting the fastening strap of the said mask,. and the other leg of which is fitted with a means of attaching it to the side parts of the mask such that the fastening points of the fastening strap are offset towards the front of the mask.

More specifically, the accepting mechanism on the leg of the angle piece is a slit in a flange which is at right angles to the said leg, and file means of attachment on the opposite leg of the angle piece consists of two hooks opening in the opposite direction and parallel to the slit, and which catch over small bars forming bracing between the front and back parts of the mask.

Other features and advantages of the invention will become apparent from the following description of a form of construction taken by way of example, in which reference is made to the attached drawings which depict:

FIG. 1: front view of a protective mask fitted with adapters

FIG. 2: plan view of the mask cut away

FIGS. 3 and 4: section and perspective views of the adapter

The protective mask shown in FIGS. 3 and 2 comprises a molded frame 1 surrounding the glass 2 and fitted with a flexible strip 3 round the entire circumference which seals the mask against the face. Air holes are provided inside the flame, blocked off by a filter plug 5. Inside the frame the air holes are separated by small bars 6 which form braces between the front and back of the mask. On each side of the mask is a slit 12 to take a fastening strap 13. As the frame is made of a relatively flexible material such as elastomer, the sides of the slit 12 possess a certain flexibility allowing the fastening bar of the strap to be inserted.

The adapter, designated as a whole under item 7, and shown in FIGS. 3 and 4, is a rigid V-shaped angle piece, one leg 8 of which has a slit 9 at one end in a flange 14 at right angles to the said leg. The opposite leg 10 of the adapter ends in two hooks 11 opening in opposite directions, parallel to the slit 9. There is a slight dissymmetry between the two legs of the adapter, the slit 9 being slightly at an angle in relation to the alignment of the hooks as shown more clearly in FIG. 4. This rigid adapter is preferably made of a plastic material such as polyamide.

When it is desired to wear a protective mask together with a helmet, the leg 10 of the adapter 7 is inserted into the slit 12 in the mask. This operation is performed by bending the edges of the adapter in relation to the slit, which is facilitated by the relative flexibility of the edges of the slit. When the leg 10 is inside the mask, the hooks 11 catch over the small bars 6. The fastening strap 13 goes through the slit 9 in the opposite leg 10, which is now positioned on the outside of the mask and well away from it. From FIG. 2 it can be seen that the place where the strap is attached is offset towards the front of the mask. When the fastening strap is placed around the helmet, tension is exerted by the strap pulling backwards on the two fastening points, thereby pressing the mask and its side pieces against the face, due to the angled shape of the adapter which compensates for the extra thickness of the helmet.

The adapter in question can either be kept straight in relation to the slit 12 in the mask, or angled, in which case one of the hooks 11 catches over a small bar 6 further away from the slit than the other.

Because of the dissymmetry of each adapter, one is required for the left side and another of the opposite orientation for the right side. Consequently they are marked so that no mistakes are made when fitting them. This dissymmetry allows for better adjustment of the mask in relation to passing the strap around the back of the helmet.

I claim:

1. An adapter in combination with a fastening strap and a protective mask for a helmet consisting of a rigid V-shaped angle piece, one end of which has a slit for securing the fastening strap for the mask and the other end of which has means of attaching to the side pieces of the mask, such that the fastening point of the fastening strap is offset towards the front of the mask, characterized by the fact that the angle piece (7) is dissymmetrical, and one leg (10) of it has two hooks (11) opening in opposite directions parallel to the slit (9) for the fastening strap, which is in a flange (14) on the other leg of the angle piece, and the hooks catch over small bars (6) which constitute bracing between the front and back of the mask.

* * * * *